United States Patent [19]

Sakurai

[11] Patent Number: 5,352,119
[45] Date of Patent: Oct. 4, 1994

[54] DISPOSABLE DENTAL PROPHY ANGLE HANDPIECE

[75] Inventor: Masatoshi Sakurai, Sakado-City, Japan

[73] Assignee: Promident Manufacturing, Limited, Saitama, Japan

[21] Appl. No.: 90,610

[22] Filed: Jul. 13, 1993

[30] Foreign Application Priority Data

May 25, 1993 [JP] Japan .................. 5-122536

[51] Int. Cl.⁵ .................................. A61C 3/06
[52] U.S. Cl. ............................. 433/125; 433/126
[58] Field of Search ............................. 433/125, 126

[56] References Cited

U.S. PATENT DOCUMENTS

| 3,163,934 | 1/1965 | Wiseman | 433/125 |
| 5,020,994 | 6/1991 | Huang | 433/125 |
| 5,028,233 | 7/1991 | Witherby | 433/125 |
| 5,224,859 | 7/1993 | Kraenzle | 433/126 |

*Primary Examiner*—John J. Wilson
*Attorney, Agent, or Firm*—Koda and Androlia

[57] ABSTRACT

A dental prophy angle handpiece used for teeth cleaning with its components made of plastic so as to be disposable after use including a front casing which comprises: foldable two sections to make a receptacle when folded, each one of the sections including a front cell, a shaft support and a cone portion formed in succession; a rotary member with a driven pinion at the middle and a metal ball at one end and installed in the front cells of the front casing; a drive shaft with a drive pinion that engages with the driven pinion of the rotary member and installed in the shaft supports of the front casing; a front cover covering the front casing to combine the front casing, the rotary member and the drive shaft into a single unit; and a cleaning cap attached to the rotary member. When the rotary member is rotated by the drive shaft that is connected to the rotary member via the pinion, the cleaning cap is rotated so as to clean the teeth.

2 Claims, 3 Drawing Sheets

DISPOSABLE DENTAL PROPHY ANGLE HANDPIECE

BACKGROUND OF THE INVENTION

1. Field of the Invention

The present invention relates to a dental handpiece and more particularly to a dental prophy angle handpiece used for cleaning teeth.

2. Prior Art

A conventional handpiece used in dental treatments, for example teeth cleaning, is a single body equipment. In other words, a dental handpiece for cleaning teeth by removing the plaque and polishing the surface of the dentin of teeth, such a handpiece being called a "prophy angle handpiece", is made of metal in a single body, and it is repeatedly used for different patients on every occasion of treatment.

Meanwhile, it has been found that the secondary infections of AIDS, hepatitis, etc. can occur during the dental treatment and the chances of secondary infections have been increased. The reason for secondary infections is believed to be the repeated use of dental equipments. Thus, it is necessary to perform an autoclave sterilization to secure the ultimate safety of the dental equipment.

However, autoclave sterilization is not always a proper cleaning method for the dental handpiece for cleaning because it comprises a great number of high precision mechanical parts including ball bearings and requires a supply of lubricant after sterilization. In addition, whether or not a sufficient lubricant is put in the handpiece cannot be verified easily.

SUMMARY OF THE INVENTION

Accordingly, the object of the present invention is to provide a dental prophy angle handpiece (hereinbelow merely called "dental handpiece") particularly to a handpiece used for teeth cleaning which is disposable and offers ample protection from the secondary infections of AIDS, hepatitis, etc. as seen in the field of dentistry.

In order to accomplish the object, the present invention provides a dental handpiece used for, for example, teeth cleaning with a unique structure that comprises a front casing consisting of a pair of sections which are hinged and formed into a receptacle when folded, a rotary member which is provided with a driven pinion and a concave end and is installed in the front casing, a drive shaft with a drive pinion at its front end so that the drive pinion is engaged with the driven pinion of the rotary member, a front cover that is mounted on the front casing so as to integrate the front casing, the rotary member and the drive shaft into a single unit, and a cleaning cap attached to the rotary member.

In this structure, the basic four components of the handpiece, which are the front casing, the rotary member, the drive shaft and the front cover are all made of plastic so that the dental handpiece can be manufactured inexpensively and therefore be disposable, thus completely avoiding the secondary infections as seen in the field of dentistry.

DETAILED DESCRIPTION OF THE INVENTION

Figure 1:
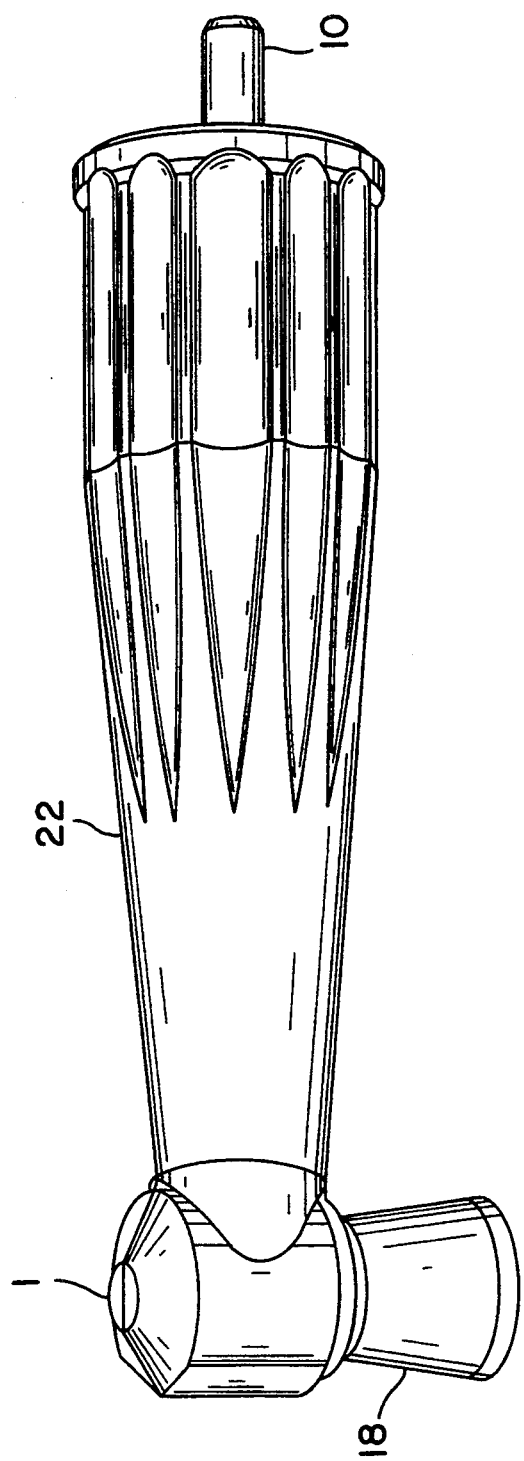
FIG. 1 is a perspective view of the dental handpiece according to the present invention.

As shown in FIG. 1, the dental handpiece of the present invention is comprised of a front casing 1 that has a cleaning cap 18, a drive shaft 10 of which the front end is brought into the front casing 1, and a front cover 22 covering the drive shaft 10 and a part of the front casing 1.

Figure 2:
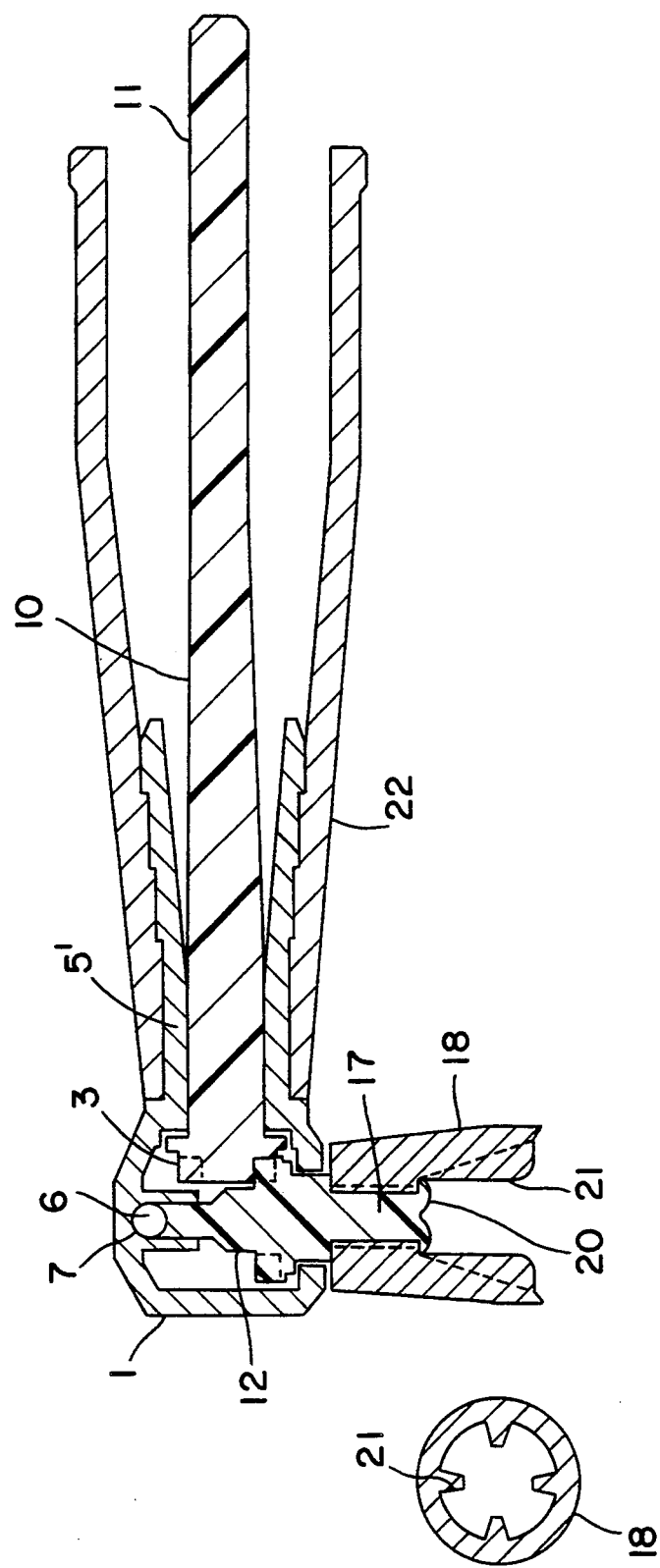
FIG. 2 is a cross section thereof.
Figure 3:
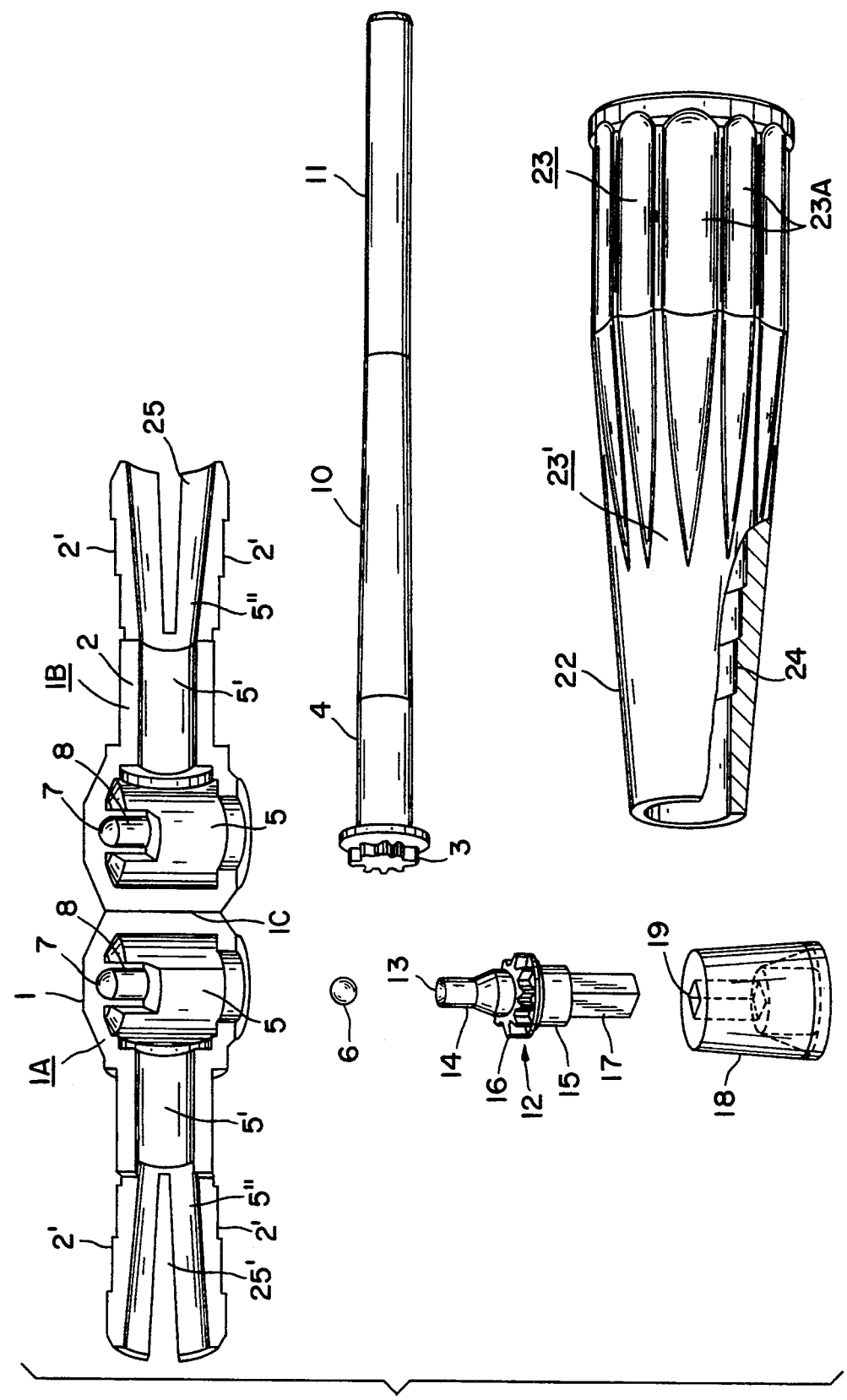
FIG. 3 shows a front casing, a drive shaft, a rotary member, a front cover and a rubber cup which are the parts and are assembled into the dental handpiece of the present invention.

More specifically, as seen from FIGS. 2 and 3, the dental handpiece for teeth cleaning according to the present invention is comprised of the front casing 1, a rotary member 12 which is installed in the front casing 1, the drive shaft 10 with its front end which has a pinion brought into the front casing 1 and is engaged with a pinion of the rotary member 12 in the front casing 1, the cleaning cap 18 which is attached to the rotary member 12, and the front cover 22 that covers the drive shaft 10 and shaft holders 5 of the front casing 1. A more detailed description of these components will be presented below.

The front casing 1, which is made of plastic, comprises a first section 1A and a second section 1B which are molded out as a single piece in which the two sections 1A and 1B are hinged at the center 1C. Thus, when the two sections 1A and 1B are closed by folding them along the center 1C, they make a receptacle for the rotary men%her 12 and the drive shaft 10.

The two sections 1A and 1B are exactly the same in shape and size. In other words, they are symmetric to each other at the center 1C. Each one of the two sections includes a front cell 5 and a shaft support 5' which is successive to the front cell 5. The front cell 5 is a vertically half cylinder shape with a shaft holder 8 formed at the center, and the top end of the shaft holder 8 is shaped into a ball holder 7 of a round shape. The shaft support 5' is a horizontally half cylinder shape with its axis perpendicular to that of the front cell 5. The shaft support 5' successively has at the end an extended half cone portion 5", and a lateral slit 25 is formed in this half cone portion 5". The slit 25 provides increased elasticity with the front casing 1.

The front cells 5, the shaft holders 5' and the cone portions 5" of the two sections 1A and 1B are surrounded by a continuous flat edge 2, and the flat edge 2 is formed with four stepped edge portions 2' near the cone portion 5".

The rotary member 12, which is also made of plastic, is provided with a driven pinion 16 at the middle and also with an upper shaft 14 and a lower shaft 15. The upper shaft 14 has a concave end 13 so that a metal ball 6 is snugly set in this concave end 13. On the other hand, the lower shaft 15 of the rotary member 12 is provided with an angled shaft 17 having, for example, a square cross section.

The drive shaft 10 is made of plastic too and includes a front end portion 4 and a rear end portion 11. A drive pinion 3 is formed on the front end surface of the front end portion 4 so that the drive pinion 3 can engage with the driven pinion 16 of the rotary member 12. The rear end portion 11 of the drive shaft 10 is connected to a power source such as an air motor, an electric motor, etc. (not shown) so that the drive shaft 10 is rotated by the power source at a specific speed.

The cleaning cap 18 is made, for example, of rubber and is substantially a hollow cylinder with somewhat a smaller top diameter and a larger bottom diameter. The cap 18 has an angled center hole 19 opened in the axial direction so that the angled shaft 17 of the rotary member 12 is brought into this hole 19. The cap 18 has a several (four in this embodiment) ridges 21 on the inner surface which extend in the axial direction of the cleaning cap 18.

The plastic-made front cover 22 is composed of a cylindrical base portion 23 and a cone shaped holding portion 23'. The base portion 23 is provided on its outer surface with a plurality of shallow round grooves 23A which extend in the axial direction so that they ensure an easy and secure holding of the handpiece in use. The holding portion 23' is provided on its inner surface with stepped grooves 24 that extend in the axial direction so that they engage with the stepped edge portions 2' of the front casing 1 when the front cover 23 is fitted over the shaft holders 5' and the cone portion 5" of the front casing 1 when assembled. The engagement provides a secure connection between the front casing 1 and the front cover 22 so that the front casing 1 is prevented from any movement in circumferential and axial directions of the front cover 22.

With the components as described above, the metal ball 6 is first placed in the concave end 13 of the rotary member 12 when assembled. Then, the rotary member 12 is installed in the front casing 1.

The rotary member 12 is fitted in one of the two front cells 5 of the two sections 1A and 1B with its upper shaft 14 being set in the shaft holder 8 and the metal ball 6 in the ball holder 7.

The drive pinion 3 of the drive shaft 10 is brought so as to engage with the driven pinion 16 of the rotary member 12.

After this, the two sections 1A and 1B of the front casing 1 is folded at the center 1C so as to be closed and to form a receptacle with the rotary member 12 and the drive pinion 3 in the front cells 5 and the front end portion 4 of the drive shaft 10 in the shaft support 5'.

Then, the front cover 22 is pushed over the shaft supports 5' and the cone portions 5" of the front casing 1 from the rear end portion 11 of the drive shaft 10 as shown, particularly, in FIG. 2. Thus, the engagement between the drive pinion 3 of the drive shaft 10 and the driven pinion 16 of the rotary member 12 is secured inside the front cells 5 of the front casing 1, so that the front casing 1, the rotary member 12 and the drive shaft 10 are integrated into a single unit.

When the front cover 22 is thus fitted on the front casing 1, the stepped edge portions 2' of the flat edge 2 are tightly fitted in the stepped grooves 24 formed on the inner surface of the front cover 22. Thus, with the lateral slits 25 and also the stepped edge portions 2' along with the elasticity of the plastic, the front casing 1 that contains the rotary member 12 and the drive shaft 10 therein is securely held inside the front cover 22, being prevented from loosening.

The cleaning cap 18 is attached to the rotary member 12 by fitting the center hole 19 of the cap 18 on the angled shaft 17 of the rotary member 12. The lower end of the angled shaft 17 is expanded by heat as shown at 20 (see FIG. 3) so that the cap 18 does not come off of the angled shaft 18. The cap 18 can be mounted to the rotary member 12 at any stage of the assembling steps. It can be mounted to the rotary member 12 before the rotary member 12 is set in one of the front cells 5.

In use of the thus assembled handpiece, the rotary shaft 10 is rotated via the power source (not show), and this rotation is transmitted to the rotary member 12 via the drive pinion 3 of the drive shaft 10 and the driven pinion 16 of the rotary member 12 which are engaged. Thus, the cap 18 is rotated by the rotating rotary member 12 so as to clean the teeth.

During the cleaning, the rotary member 12 is rotated smoothly with the help of the metal ball 6 mounted thereon since the metal ball 6 can reduce the frictional resistance which is caused by the fluctuating load mainly in the thrust direction during the cleaning operation. In addition, the metal ball 6 which is snugly set in the concave end 13 of the upper shaft 14 can provide a centripetal force with the rotary member 12 for the smooth rotation of the rotary member 12.

Furthermore, since the components of the dental handpiece of this invention are made of plastic except for the metal ball 6 and the rubber cap 18, the handpiece is light in weight and has an appropriate elasticity that provides a tight engagement of the components and can absorb vibrations; accordingly, teeth cleaning can be performed smoothly. In addition, the handpiece can be manufactured at a lower cost, assembled easily and disposed after use.

As seen from the above, the present invention provides a disposable dental handpiece used for, for example, teeth cleaning, thus it assures hygiene and safety and prevents the secondary infections of AIDS, hepatitis, etc. in dentistry. The invention is described in conjunction with the one for teeth cleaning with the use of the cleaning cap; however, the dental handpiece of the present invention can be used in other types of dental operations by replacing the cleaning cap in other dental attachments.

I claim:

1. A dental prophy angle handpiece comprising:
    a front casing comprising two sections which are hinged at its center so as to make a receptacle when folded, each of said sections including a front cell, a shaft support and a coned portion which are formed successively;
    a rotary member installed in said front casing, said rotary member being provided with a driven pinion at its middle portion, a concave end at one end and an angled shaft at another end;
    a metal ball placed in said concave end of said rotary member;
    a drive shaft provided with a drive pinion on an end surface, one end of said drive shaft being set in said shaft holders of said front casing and said drive pinion being engaged with said driven pinion of said rotary member in said front cells of said front casing;
    a front cover mounted on said front casing forming said rotary member, drive shaft and front casing into a single unit;
    flat edges formed around said front cells, shaft supports and cone portions of said front casing; and
    a cleaning cap attached to said angled shaft of said rotary member; and wherein
    said front casing, rotary member, drive shaft and front cover are made of plastic; and
    said flat edges are provided with stepped edge portions and said front cover is provided with stepped grooves on its inner surface so that said stepped edges portions and said stepped grooves are engaged with each other.

2. A dental prophy angle handpiece according to claim 1, wherein each one of said front cells of said front casing is provided with a shaft holder which is further provided with a ball holder at one end so that said concave end is positioned in said shaft holder and said metal ball is positioned in said ball holder.

* * * * *